United States Patent [19]

Bearce

[11] Patent Number: 4,770,041

[45] Date of Patent: Sep. 13, 1988

[54] APPARATUS FOR DETERMINING SPECIFIC GRAVITY AND DENSITY

[76] Inventor: Peter J. Bearce, 51792 E. National Rd., St. Clairsville, Ohio 43950

[21] Appl. No.: 158,844

[22] Filed: Feb. 22, 1988

[51] Int. Cl.[4] ............................ G01N 9/10; G01G 5/02
[52] U.S. Cl. ........................................ 73/437; 177/207
[58] Field of Search .................... 177/207; 73/435–437

[56] References Cited

U.S. PATENT DOCUMENTS

| | | | |
|---|---|---|---|
| 2,650,494 | 9/1953 | Linhorst | 73/437 |
| 3,747,416 | 7/1973 | Wommack | 73/437 |
| 3,871,489 | 3/1975 | Patigalia | 177/207 X |
| 3,991,619 | 11/1976 | Appleford et al. | 73/437 |
| 4,320,658 | 3/1982 | Hilton et al. | 73/437 |
| 4,372,405 | 2/1983 | Stuart | 177/207 X |

FOREIGN PATENT DOCUMENTS 0016536 of 1909 United Kingdom ................ 73/437

Primary Examiner—George H. Miller, Jr.
Attorney, Agent, or Firm—William J. Ruano

[57] ABSTRACT

Apparatus for weighing a specimen while suspended in water to determine its specific gravity. A scale is mounted on a table. A rectangular frame having legs surrounding the scale is supported on the table. A liquid filled container is supported directly on the rectangular frame. A second rectangular frame having legs supported directly on the scale has its legs extending through the top of the first mentioned rectangular frame without contact with the top. A specimen is suspended by suspension means from the top of the second rectangular frame to the liquid in the container so that its weight and that of the second rectangular frame and suspension means are the only weights borne directly by the scale.

2 Claims, 1 Drawing Sheet

APPARATUS FOR DETERMINING SPECIFIC GRAVITY AND DENSITY

This invention relates to apparatus for weighing a specimen while suspended in water to determine its specific gravity.

BACKGROUND OF THE INVENTION

Apparatus for weighing a specimen suspended in water have been used in the past but have required the formation of holes in a table for inserting suspending means for a specimen suspended in a large tub of water supported on a floor. This has required not only a large container of water but the necessity of extending suspending means through openings in a table and tying up a scale and assembly restricted only to this type of measurement.

SUMMARY OF THE INVENTION

An object of the present invention is to overcome the above-named disadvantages of presently used apparatus and to avoid the necessity of forming holes in a table or of supporting the specimen in a container supported on a floor, also to free the use of electronic scales for any weighing purposes. The present invention comprises an assembly which is portable and which can be laid on top of the scale and above the top of the table including the container holding the specimen in suspension.

DESCRIPTION OF THE PREFERRED EMBODIMENT

Figure 1:
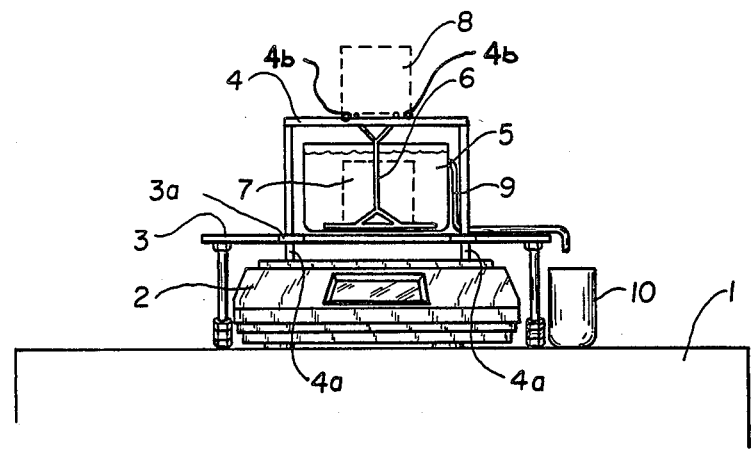
FIG. 1 is an elevational view of a table on which is mounted the apparatus of the present invention.
Figure 2:
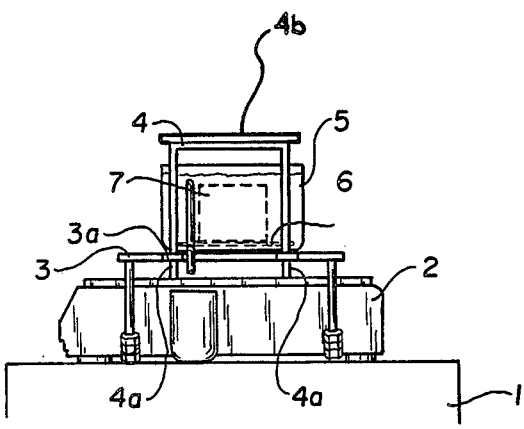
FIG. 2 is a side view thereof.
Figure 3:
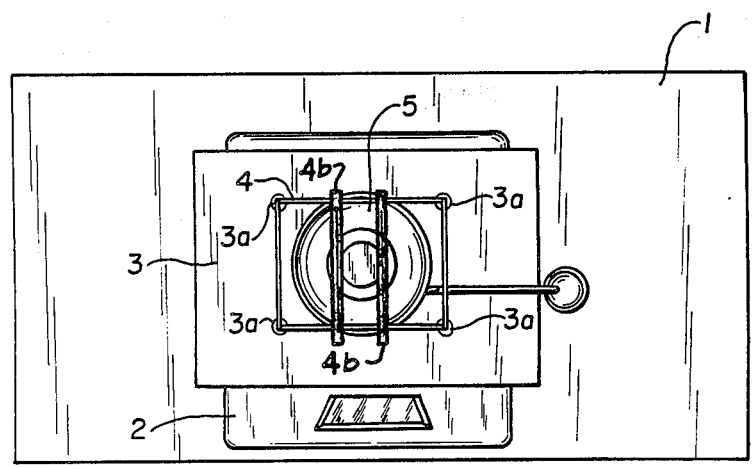
FIG. 3 is a top view thereof

Referring to FIGS. 1, 2 and 3 of the drawing, numeral 1 denotes an ordinary work table and numeral 2 denotes an electronic weighing scale of any well known type such as one having a digital readout.

The present invention comprises a rectangular frame 3 having four legs supported on table 1 and having a horizontal, rectangular portion as appears in FIG. 3.

Resting directly on the scale 2 is a second rectangular frame 4 having four legs which extend through holes 3a in frame 3 with adequate clearance so as to enable the lower ends 4a, 4a of the frame to rest directly on the scale 2. Resting on top of frame 4 are two beams, 4b, 4b which can be positioned close enough together to support specimen 8 well above container 5 allowing the apparatus to indicate the weight of specimen 8 in air. Beams 4b, 4b can then be removed altogether, or they can be slid apart far enough to enable the user to introduce specimen 8 into container 5 as indicated by numeral 7.

Supported on the top of table 3 is a container 5 having water maintained at the level indicated by means of an overflow outlet 9 leading to a container 10.

Suspended from the top of the frame or second table 4 and centrally at the top by means of a cord 6 is a specimen 7 whose specific gravity is to be determined such as one of molded bituminous mixture such as from a bituminous pavement.

In operation, the specimen 7 is in suspension in a liquid and is weighed directly by the scale 2 together with the frame 4 and suspending cord 6 which frame and suspending cord are zeroed in the scale so that the scale indicates only the weight of the specimen.

Thus it will be seen that I have provided a novel assembly for weighing a specimen suspended in a liquid that eliminates the necessity for forming holes in a table or for supporting a large container on a floor or for tying up a scale for use only for a single purpose instead of for other uses as well.

While I have illustrated and described several embodiments of my invention, it will be understood that these are by way of illustration only and that various changes and modifications may be contemplated in my invention and within the scope of the following claims.

I claim:

1. In combination with a scale mounted on a table, a rectangular frame having legs surrounding said scale and supported on said table, a liquid containing container supported directly on said rectangular frame, a second rectangular frame having legs supported directly on said scale and extending through the top of said first mentioned rectangular frame without contacting said top, a specimen, suspension means suspending said specimen from the top of said second rectangular frame to said liquid containing container so that its weight and that of said second rectangular frame and said suspension means are the only weights borne by said scale.

2. The combination recited in claim 1 wherein said first mentioned rectangular frame has a table top having holes through which the legs of said second rectangular frame extend without contacting said first mentioned rectangular frame.

* * * * *